(12) United States Patent
Halverson et al.

(10) Patent No.: US 11,833,267 B2
(45) Date of Patent: Dec. 5, 2023

(54) METHODS FOR DEVELOPING POROUS IMPLANTS OF OPTIMAL PROPERTIES

(71) Applicant: Nexus Spine, LLC, Salt Lake City, UT (US)

(72) Inventors: Peter Halverson, Draper, UT (US); David T. Hawkes, Pleasant Grove, UT (US)

(73) Assignee: Nexus Spine, LLC, Salt Lake City, UT (US)

( * ) Notice: Subject to any disclaimer, the term of this patent is extended or adjusted under 35 U.S.C. 154(b) by 910 days.

(21) Appl. No.: 16/813,720

(22) Filed: Mar. 9, 2020

(65) Prior Publication Data
US 2020/0286593 A1 Sep. 10, 2020

Related U.S. Application Data

(60) Provisional application No. 62/815,259, filed on Mar. 7, 2019.

(51) Int. Cl.
| | |
|---|---|
| *A61L 27/56* | (2006.01) |
| *G16C 20/30* | (2019.01) |
| *B33Y 50/00* | (2015.01) |
| *G06T 19/20* | (2011.01) |
| *B33Y 80/00* | (2015.01) |

(Continued)

(52) U.S. Cl.
CPC ............ *A61L 27/06* (2013.01); *A61L 27/365* (2013.01); *A61L 27/56* (2013.01); *B22F 10/38* (2021.01); *B33Y 50/00* (2014.12); *G06T 19/20* (2013.01); *G16C 20/10* (2019.02); *G16C 20/30* (2019.02); *A61L 2420/02* (2013.01);

(Continued)

(58) Field of Classification Search
CPC ..... A61L 27/56; A61L 2430/02; B33Y 50/00; B33Y 80/00; G06T 19/20; G06T 2219/2021; G16C 20/10; G16C 20/30
See application file for complete search history.

(56) References Cited

PUBLICATIONS

Saravana Kumar, G., & George, S. P. (2017). Optimization of custom cementless stem using finite element analysis and elastic modulus distribution for reducing stress-shielding effect. Proceedings of the Institution of Mechanical Engineers, Part H: Journal of Engineering in Medicine, 231(2), 149-159. (Year: 2017).*

(Continued)

*Primary Examiner* — Bijan Mapar
(74) *Attorney, Agent, or Firm* — Bryant J. Keller; Kirton McConkie (57) ABSTRACT

A porous implant design method includes defining a design volume for a porous implant, a load to be borne by the design volume, and an objective function solution characteristic related to the design volume. Next, the load is divided into a plurality of sub-loads and an optimization procedure is performed: until all sub-loads have been applied, one of the plurality of sub-loads is applied to the material in the design volume, material from the design volume is removed such that remaining material within the design volume is capable of bearing one of the plurality of sub-loads while satisfying the objection function solution characteristic; the remaining material defines a void space without material, the void space is set as a new design volume for any remaining sub-loads, the new design volume is set as being full of material. Then, the remaining material from each cycle of the optimization is combined.

20 Claims, 6 Drawing Sheets

(51) Int. Cl.
    *A61L 27/06*     (2006.01)
    *G16C 20/10*     (2019.01)
    *A61L 27/36*     (2006.01)
    *B22F 10/38*     (2021.01)
    *B22F 10/20*     (2021.01)

(52) U.S. Cl.
    CPC ........... *A61L 2430/02* (2013.01); *B22F 10/20* (2021.01); *B33Y 80/00* (2014.12); *G06T 2219/2021* (2013.01)

(56) References Cited

PUBLICATIONS

Kang, H., Long, J. P., Goldner, G. D. U., Goldstein, S. A., & Hollister, S. J. (2012). A paradigm for the development and evaluation of novel implant topologies for bone fixation: implant design and fabrication. Journal of biomechanics, 45(13), 2241-2247. (Year: 2012).*

* cited by examiner

METHODS FOR DEVELOPING POROUS IMPLANTS OF OPTIMAL PROPERTIES

CROSS-REFERENCE TO RELATED APPLICATIONS

This application claims the benefit of U.S. Provisional Application No. 62/815,256, filed Mar. 7, 2019.

BACKGROUND OF THE INVENTION

1. Field of the Invention

The present invention relates to designing porous implants, and more particularly to systems and methods for developing porous implants of optimal properties.

2. Background and Related Art

Orthopedic implants are often made porous with a goal of promoting ongrowth of bone to the implant as well as ingrowth of the bone into the porous structure of the implant. Implants are typically manufactured of biocompatible materials. Unfortunately, the majority of manmade materials that are biocompatible and from which implants can be constructed have bulk characteristics that are significantly different from the physical characteristics of bone.

Human bones are generally formed of two types of structural bone tissue: cortical bone and trabecular or cancellous bone. Cortical bone generally forms the outer shell of most bones, and is more dense, harder, stronger, and stiffer than trabecular bone. Trabecular bone is typically found at the ends of long bones proximal to joints, as well as in the interior of vertebrae. Trabecular bone is highly vascularized and has a generally porous or spongy structure through which blood vessels pass. Generally, trabecular bone has pores that are on the order of 150 to 650 microns in size. Not all trabecular bone has the same porosity; different bones have different trabecular bone porosity.

The physical characteristics of bone are important for physiological purposes related to the growth and formation of bone both originally as well as during the healing process. The cells responsible for bone growth, including osteocytes and osteoblasts, work together to form bone as needed within the body, but will only form bone under proper conditions, including when the cells experience proper loads and stresses, when a network of blood vessels is available to supply needed nutrients, and when gaps to be filled by bone are of a proper size. When proper conditions are not available, bone cannot or will not grow. For example, when bone does not experience loading, it will not grow and can even be resorbed. Additionally, when gaps to be filled are too large or too small, bone cannot bridge the gap and will not grow.

In addition to proper physical conditions, bone growth only occurs when certain conditions are met. First, there must be a kernel of living bone to start the process. The living bone supplies the cells necessary for bone growth and formation. Additionally, a cascade of chemical triggers is required for bone to grow. Finally, because bone growth is impeded by the presence of certain materials and/or chemicals, an absence of such materials and chemicals is required for proper bone growth.

One example of where it is generally recognized as advantageous to promote bone growth is in the orthopedic implant industry. One goal with many orthopedic implants is for bone growth at the interface to fuse or secure the implant to the bone. For this reason, many orthopedic implants are provided with a porous surface at the bone-implant interface, with the expectation that bone will grow onto and into the porous surface of the implant. Other implants may be provided with one or more cavities or voids to receive bone growth (e.g., a graft window), and during surgery any such cavities or voids may be filled with a material intended to promote bone growth, including morcellized bone graft material. These techniques have been used in implants for years with varying degrees of success, but the success of such devices has been limited by the devices' ongoing failure to provide physical and chemical characteristics most conducive to bone growth. Even when a graft is present in a cavity or void, any bone that does form on or around the device is of lesser quality and quantity.

Generally, current implants have one or more characteristics that are not maximally conducive to facilitating bone growth into the implant. For example, some implants may provide a pore size that is generally within a desirable range, but may have a stiffness that is too high to allow bone within the porous structure of the implant to be properly loaded. As a result, the bone will not take advantage of the correct porosity and pore size of such implants, and will grow only minimally, if at all, in the porous structure of such implants. In other implants, the stiffness may be generally within a desirable range, but in order to achieve the desired stiffness, the device manufacturer creates pores that are too large or too small to facilitate proper bone growth. As a result, while the bone cells can be properly loaded, they are unable to grow bone in the available pores.

Some manufacturers have used the material polyetheretherketone (PEEK) in orthopedic implants, as PEEK has a bulk stiffness (4 gigapascals (GPa)) that is close to that of bone (0.3 GPa<bone stiffness<4 GPa). Unfortunately, PEEK is not chemically a bone-friendly material. As a result, when PEEK is used for implants, a fibrous layer is formed by the body around the implant to protect the body from the PEEK, and bone growth does not occur. Other commonly used materials are titanium and tantalum, which are osteoconductive but have a relatively high bulk stiffness (approximately 116 GPa) that shields the bone from appropriate mechanical stimulus necessary for proper bone growth. Stainless steel, another possible implant material, is not very osteoconductive and also has a very high bulk stiffness (approximately 210 GPa).

Many currently available implants made of titanium have a stiffness that approaches the stiffness of a block of solid titanium. These devices are typically too stiff even in their porous regions. Additionally, many devices have porous regions contained within a solid surrounding structure that prevents the intervening porous region from being loaded in a way conducive to bone growth. Trabecular metal is one of the least stiff predicate materials that is still more than twice as stiff as the maximum desired stiffness desired to promote bone growth through proper loading.

One particular type of implant that is illustrative of the difficulties encountered with predicate devices is an interbody spacer intended for placement between vertebral bodies in spinal fusion procedures. Predicate devices have focused almost exclusively on providing support for the spine, giving little to no attention to promoting or stimulating bone growth. As a result, while such devices may achieve bone on-growth at the surface of the device, such devices do not achieve ingrowth that extends throughout the devices.

For example, the TM-S® cervical fusion device and the TM Ardis® interbody system by Zimmer Biomet are made using elemental tantalum ("trabecular metal") and achieve a pore size on the order of 550 microns. Despite having a pore size that is generally within the desired range, the stiffness of the implant is determined by the size and shape of the material between the pores, and remains at least twice and as much as ten times the desired stiffness. Due to the lack of proper loading, bone does not grow within the Zimmer devices to a significant extent.

Similarly, Stryker's Tritanium® PL posterior lumbar cage has a pore size of 616 microns, only slightly exceeding the desired pore size. Again, however, the device's stiffness is determined by the size and shape of the material between the pores and at the margins of the device itself. As a result, any bone that does enter the pores of the device cannot be properly loaded, and ingrowth does not occur. The stiffness of the Stryker device may exceed the stiffness of the Zimmer devices.

Other devices, such as the 4WEB® Medical Spine Truss system, the K2M Cascadia™ devices, the Titan Endoskeleton® TO device, and the Signus-Mobis® II ST devices all have even larger pore sizes as well as portions of solid non-porous titanium along leading and trailing edges of the devices. Thus, even if portions of such devices have a stiffness that is generally correct, such portions cannot be loaded due to the solid portions of the devices. The lack of loading prevents bone growth in the interior of the devices. Additionally, the large pore sizes (e.g., on the order of greater than 1700 microns) cannot be bridged by bone.

Thus, there remains an unmet need in the orthopedic implant industry for implants that provide stiffness and pore sizes that are conducive to bone growth using materials that are also conducive to bone growth. This need is especially felt in the spinal implant industry, for example with respect to interbody spacers.

BRIEF SUMMARY OF THE INVENTION

Implementation of the invention provides systems, methods (including computer-implemented methods), and non-transitory computer-readable media for causing computer systems to implement methods for developing porous implants of optimal physical properties such as stiffness and porosity. Additionally, implementations of the invention provide implants designed in accordance with the systems and methods disclosed herein. Implementations of the invention address the deficiencies with previous porous implants, providing implants designed to have a stiffness and a porosity (or other physical characteristics) within a desired range to satisfy the design demands to allow the implants to perform a desired function. More specifically, implementations of the invention provide porous implants having desired physical characteristics to provide, for example, conditions conducive to bone ingrowth and ongrowth.

According to implementations of the invention, a method for developing a porous implant includes steps of defining a design volume for a porous implant, defining a load to be borne by the design volume of the porous implant, and defining an objective function solution characteristic related to the design volume of the porous implant. The method further includes steps of dividing the load into a plurality of sub-loads and performing an optimization procedure. The optimization procedure includes performing, until all sub-loads have been applied, repeated steps of applying one of the plurality of sub-loads to the material in the design volume, removing material from the design volume such that remaining material within the design volume is capable of bearing one of the plurality of sub-loads and satisfies the objection function solution characteristic, the remaining material defining a void space without material therein, setting the void space as a new design volume for any remaining sub-loads, and setting the new design volume as being full of material. The method further includes a final step of combining the remaining material from each cycle of the optimization as a design of the porous implant.

In some implementations, the steps of applying one of the plurality of sub-loads and removing material from the design volume include performing a finite element analysis. In some implementations, the steps of applying one of the plurality of sub-loads and removing material from the design volume include finding a closed form solution. In some implementations, the method is performed on a computer system.

In some implementations, the objective function solution characteristic includes maximizing or minimizing a characteristic such as stress, mass, surface area, radiolucency, or stiffness. In some implementations, the repeated steps of the optimization procedure further include dilating the new design volume to create a buffer region to ensure a desired porosity in the boundary between the material from each cycle of the optimization.

In some implementations, the method also includes performing a final evaluation and optimization for a different objective function. In some implementations, the different objective function is a function such as weight, porosity, surface area, or stress. In some implementations, the design volume is pre-divided into a plurality of design volumes, each with its own portion of the load to be borne; the method is performed in parallel with respect to each of the plurality of design volumes and portions of the load to be borne.

According to further implementations, a computer-implemented method for developing a porous implant includes steps of defining a design volume for a porous implant, defining a load to be borne by the design volume of the porous implant, and defining an objective function solution characteristic related to the design volume of the porous implant. The method further includes using a computing device to divide the load into a plurality of sub-loads and causing the computing device to perform an optimization procedure. The optimization procedure includes performing, until all sub-loads have been applied, repeated steps of applying one of the plurality of sub-loads to the material in the design volume, removing material from the design volume such that remaining material within the design volume is capable of bearing one of the plurality of sub-loads and satisfies the objection function solution characteristic, the remaining material defining a void space without material therein, setting the void space as a new design volume for any remaining sub-loads, and setting the new design volume as being full of material. The method also includes a final step of combining the remaining material from each cycle of the optimization as a design of the porous implant.

In some implementations, the steps of applying one of the plurality of sub-loads and removing material from the design volume include performing a finite element analysis. In some implementations, the steps of applying one of the plurality of sub-loads and removing material from the design volume include finding a closed form solution.

In some implementations, the objective function solution characteristic includes maximizing or minimizing a characteristic such as stress, mass, surface area, radiolucency, or stiffness. In some implementations, the repeated steps of the optimization procedure further include dilating the new design volume to create a buffer region to ensure a desired porosity in the boundary between the material from each cycle of the optimization. In some implementations, the method further includes performing a final evaluation and optimization for a different objective function such as weight, porosity, surface area, or stress. In some implementations, the design volume is pre-divided into a plurality of design volumes; the method is performed in parallel with respect to each of the plurality of design volumes and portions of the load to be borne.

According to additional implementations, a computer-implemented method for developing a porous implant includes steps of defining a design volume for a porous implant, defining a load to be borne by the design volume of the porous implant, and defining an objective function solution characteristic related to the design volume of the porous implant, the objective function solution characteristic including maximizing or minimizing a characteristic such as stress, mass, surface area, radiolucency, or stiffness. The method further includes using a computing device to divide the load into a plurality of sub-loads and causing the computing device to perform an optimization procedure including performing, until all sub-loads have been applied, repeated steps of applying one of the plurality of sub-loads to the material in the design volume, removing material from the design volume such that remaining material within the design volume is capable of bearing one of the plurality of sub-loads and satisfies the objection function solution characteristic, the remaining material defining a void space without material therein, setting the void space as a new design volume for any remaining sub-loads, and setting the new design volume as being full of material. The method also includes a final step of combining the remaining material from each cycle of the optimization as a design of the porous implant.

In some implementations, the repeated steps of the optimization procedure further include dilating the new design volume to create a buffer region to ensure a desired porosity in the boundary between the material from each cycle of the optimization. In some implementations, the method further includes performing a final evaluation and optimization for a different objective function such as weight, porosity, surface area, or stress. In some implementations, the design volume is pre-divided into a plurality of design volumes, each with its own portion of the load to be borne; the method is performed in parallel with respect to each of the plurality of design volumes and portions of the load to be borne.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide systems, methods (including computer-implemented methods), and non-transitory computer-readable media for causing computer systems to implement methods for developing porous implants of optimal physical properties such as stiffness and porosity. Additionally, embodiments of the invention provide implants designed in accordance with the systems and methods disclosed herein. Embodiments of the invention address the deficiencies with previous porous implants, providing implants designed to have a stiffness and a porosity (or other physical characteristics) within a desired range to satisfy the design demands to allow the implants to perform a desired function. More specifically, embodiments of the invention provide porous implants having desired physical characteristics to provide, for example, conditions conducive to bone ingrowth and ongrowth.

According to embodiments of the invention, a method for developing a porous implant includes steps of defining a design volume for a porous implant, defining a load to be borne by the design volume of the porous implant, and defining an objective function solution characteristic related to the design volume of the porous implant. The method further includes steps of dividing the load into a plurality of sub-loads and performing an optimization procedure. The optimization procedure includes performing, until all sub-loads have been applied, repeated steps of applying one of the plurality of sub-loads to the material in the design volume, removing material from the design volume such that remaining material within the design volume is capable of bearing one of the plurality of sub-loads and satisfies the objection function solution characteristic, the remaining material defining a void space without material therein, setting the void space as a new design volume for any remaining sub-loads, and setting the new design volume as being full of material. The method further includes a final step of combining the remaining material from each cycle of the optimization as a design of the porous implant.

In some embodiments, the steps of applying one of the plurality of sub-loads and removing material from the design volume include performing a finite element analysis. In some embodiments, the steps of applying one of the plurality of sub-loads and removing material from the design volume include finding a closed form solution. In some embodiments, the method is performed on a computer system.

In some embodiments, the objective function solution characteristic includes maximizing or minimizing a characteristic such as stress, mass, surface area, radiolucency, or stiffness. In some embodiments, the repeated steps of the optimization procedure further include dilating the new design volume to create a buffer region to ensure a desired porosity in the boundary between the material from each cycle of the optimization.

In some embodiments, the method also includes performing a final evaluation and optimization for a different objective function. In some embodiments, the different objective function is a function such as weight, porosity, surface area, or stress. In some embodiments, the design volume is pre-divided into a plurality of design volumes, each with its own portion of the load to be borne; the method is performed in parallel with respect to each of the plurality of design volumes and portions of the load to be borne.

According to further embodiments, a computer-implemented method for developing a porous implant includes steps of defining a design volume for a porous implant, defining a load to be borne by the design volume of the porous implant, and defining an objective function solution characteristic related to the design volume of the porous implant. The method further includes using a computing device to divide the load into a plurality of sub-loads and causing the computing device to perform an optimization procedure. The optimization procedure includes performing, until all sub-loads have been applied, repeated steps of applying one of the plurality of sub-loads to the material in the design volume, removing material from the design volume such that remaining material within the design volume is capable of bearing one of the plurality of sub-loads and satisfies the objection function solution characteristic, the remaining material defining a void space without material therein, setting the void space as a new design volume for any remaining sub-loads, and setting the new design volume as being full of material. The method also includes a final step of combining the remaining material from each cycle of the optimization as a design of the porous implant.

In some embodiments, the steps of applying one of the plurality of sub-loads and removing material from the design volume include performing a finite element analysis. In some embodiments, the steps of applying one of the plurality of sub-loads and removing material from the design volume include finding a closed form solution.

In some embodiments, the objective function solution characteristic includes maximizing or minimizing a characteristic such as stress, mass, surface area, radiolucency, or stiffness. In some embodiments, the repeated steps of the optimization procedure further include dilating the new design volume to create a buffer region to ensure a desired porosity in the boundary between the material from each cycle of the optimization. In some embodiments, the method further includes performing a final evaluation and optimization for a different objective function such as weight, porosity, surface area, or stress. In some embodiments, the design volume is pre-divided into a plurality of design volumes; the method is performed in parallel with respect to each of the plurality of design volumes and portions of the load to be borne.

According to additional embodiments, a computer-implemented method for developing a porous implant includes steps of defining a design volume for a porous implant, defining a load to be borne by the design volume of the porous implant, and defining an objective function solution characteristic related to the design volume of the porous implant, the objective function solution characteristic including maximizing or minimizing a characteristic such as stress, mass, surface area, radiolucency, or stiffness. The method further includes using a computing device to divide the load into a plurality of sub-loads and causing the computing device to perform an optimization procedure including performing, until all sub-loads have been applied, repeated steps of applying one of the plurality of sub-loads to the material in the design volume, removing material from the design volume such that remaining material within the design volume is capable of bearing one of the plurality of sub-loads and satisfies the objection function solution characteristic, the remaining material defining a void space without material therein, setting the void space as a new design volume for any remaining sub-loads, and setting the new design volume as being full of material. The method also includes a final step of combining the remaining material from each cycle of the optimization as a design of the porous implant.

In some embodiments, the repeated steps of the optimization procedure further include dilating the new design volume to create a buffer region to ensure a desired porosity in the boundary between the material from each cycle of the optimization. In some embodiments, the method further includes performing a final evaluation and optimization for a different objective function such as weight, porosity, surface area, or stress. In some embodiments, the design volume is pre-divided into a plurality of design volumes, each with its own portion of the load to be borne; the method is performed in parallel with respect to each of the plurality of design volumes and portions of the load to be borne.

Figure 1:
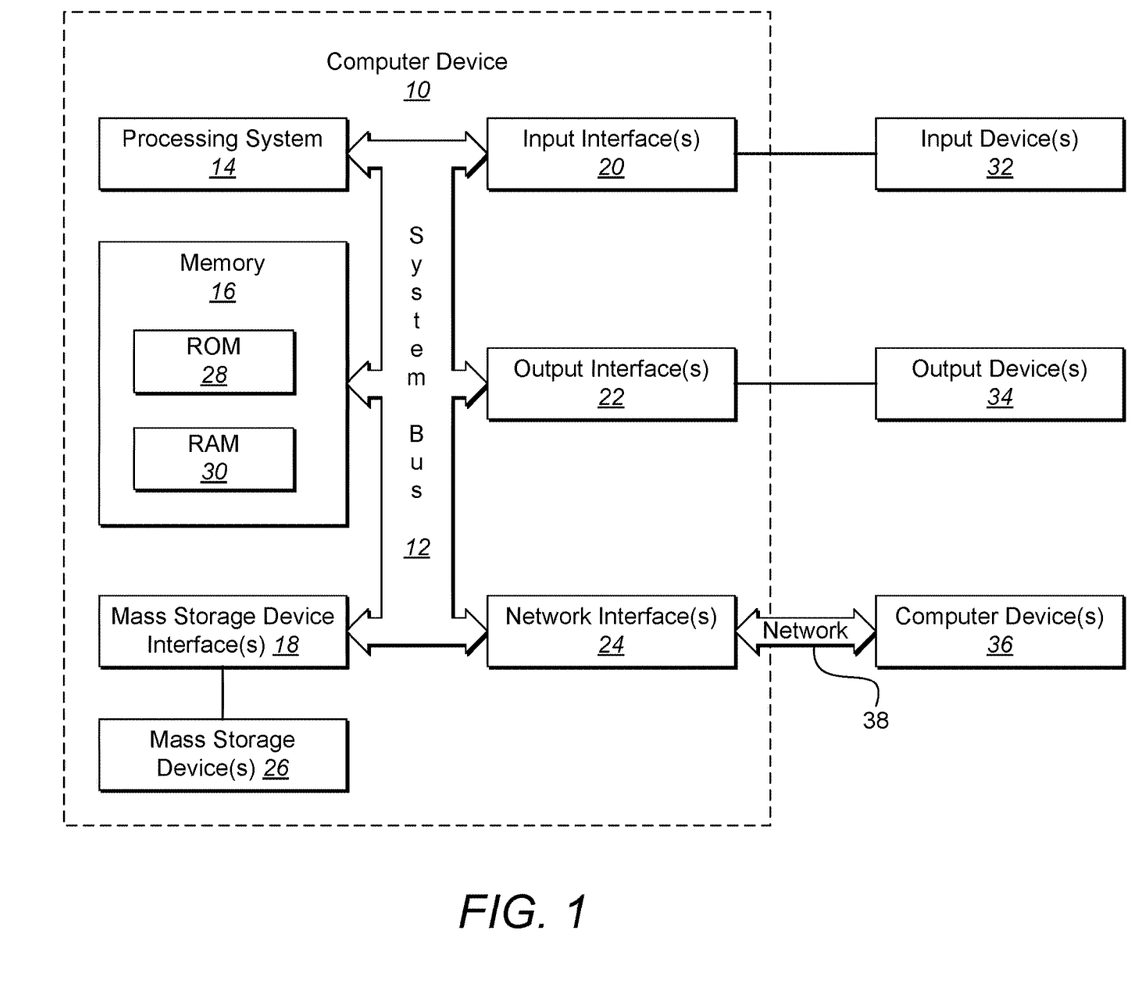
FIG. 1 shows a representative computer system in which embodiments of the invention may be implemented.

FIG. 1 and the corresponding discussion are intended to provide a general description of a suitable operating environment in which embodiments of the invention may be implemented. One skilled in the art will appreciate that embodiments of the invention may be practiced by one or more computing devices and in a variety of system configurations, including in a networked configuration. However, while the methods and processes of the present invention have proven to be particularly useful in association with a system comprising a general purpose computer, embodiments of the present invention include utilization of the methods and processes in a variety of environments, including embedded systems with general purpose processing units, digital/media signal processors (DSP/MSP), application specific integrated circuits (ASIC), stand alone electronic devices, and other such electronic environments.

Embodiments of the present invention embrace one or more computer-readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. While embodiments of the invention embrace the use of all types of computer-readable media, certain embodiments as recited in the claims may be limited to the use of tangible, non-transitory computer-readable media, and the phrases "tangible computer-readable medium" and "non-transitory computer-readable medium" (or plural variations) used herein are intended to exclude transitory propagating signals per se.

With reference to FIG. 1, a representative system for implementing embodiments of the invention includes computer device 10, which may be a general-purpose or special-purpose computer or any of a variety of consumer electronic devices. For example, computer device 10 may be a personal computer, a notebook or laptop computer, a netbook, a personal digital assistant ("PDA") or other hand-held device, a smart phone, a tablet computer, a workstation, a minicomputer, a mainframe, a supercomputer, a multi-processor system, a network computer, a processor-based consumer electronic device, a computer device integrated into another device or vehicle, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer-readable media, such as on memory 16, a solid state drive, a removable solid state drive, a magnetic hard disk, a removable magnetic disk, a magnetic cassette, an optical disk, or from a communication connection, which may also be viewed as a computer-readable medium.

Memory 16 includes one or more computer-readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include solid state drives, hard disk drives, magnetic disk drives, tape drives and optical disk drives. A mass storage device 26 may read from and/or write to solid state memory, a magnetic hard disk, a removable magnetic disk, a magnetic cassette, an optical disk, or another computer-readable medium. Mass storage devices 26 and their corresponding computer-readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a firewire (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen, a speaker, a printer, a multi-functional peripheral, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Figure 2:
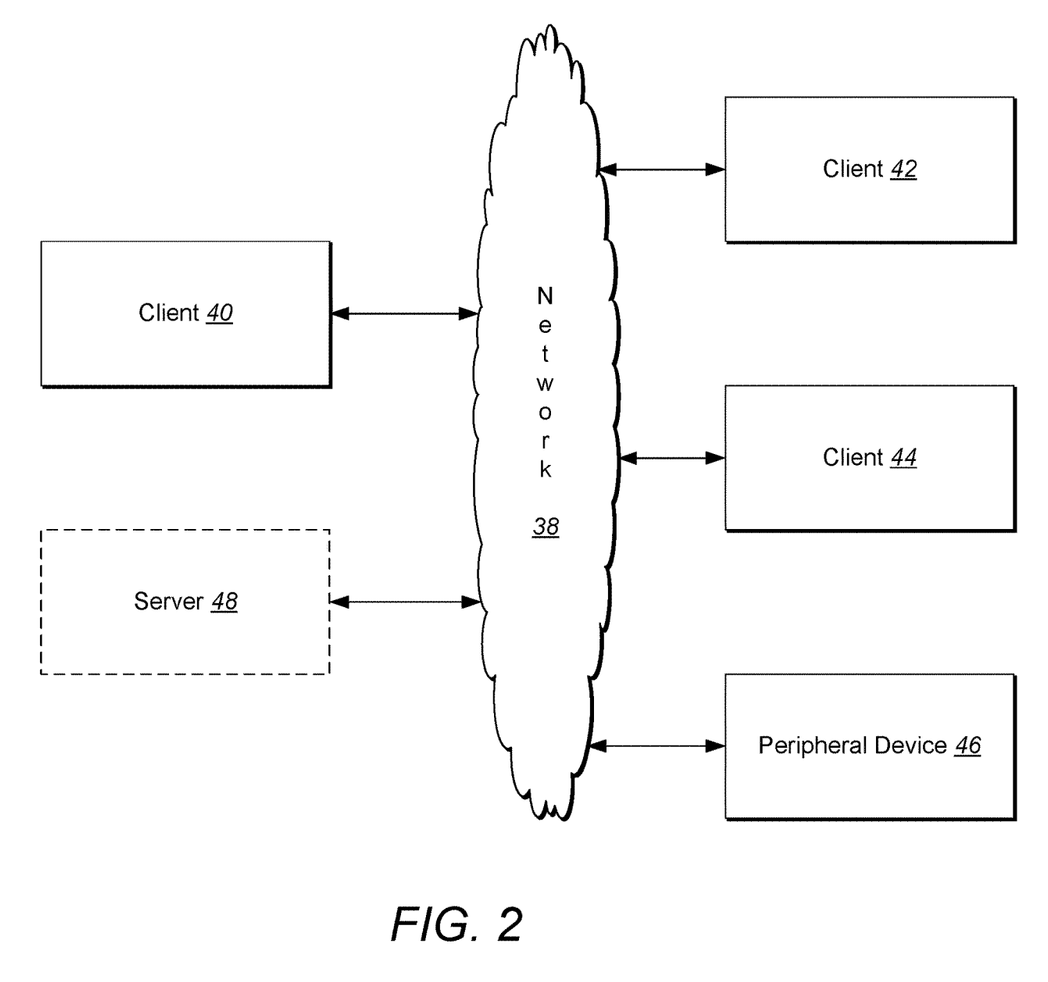
FIG. 2 shows a representative networked computer system in which embodiments of the invention may be implemented.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices 46 across network 38. While FIG. 2 illustrates an embodiment that includes a client 40, two additional clients, client 42 and client 44, one peripheral device 46 (such as a 3D printer), and optionally a server 48, which may be a print server, connected to network 38, alternative embodiments include more or fewer clients, more than one peripheral device, no peripheral devices, no server 48, and/or more than one server 48 connected to network 38. Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet.

Similarly, embodiments of the invention embrace cloud-based architectures where one or more computer functions are performed by remote computer systems and devices at the request of a local computer device. Thus, returning to FIG. 2, the client 40 may be a computer device having a limited set of hardware and/or software resources. Because the client 40 is connected to the network 38, it may be able to access hardware and/or software resources provided across the network 38 by other computer devices and resources, such as client 42, client 44, server 48, or any other resources. The client 40 may access these resources through an access program, such as a web browser, and the results of any computer functions or resources may be delivered through the access program to the user of the client 40. In such configurations, the client 40 may be any type of computer device or electronic device discussed above or known to the world of cloud computing, including traditional desktop and laptop computers, smart phones and other smart devices, tablet computers, or any other device able to provide access to remote computing resources through an access program such as a browser.

Figure 3:
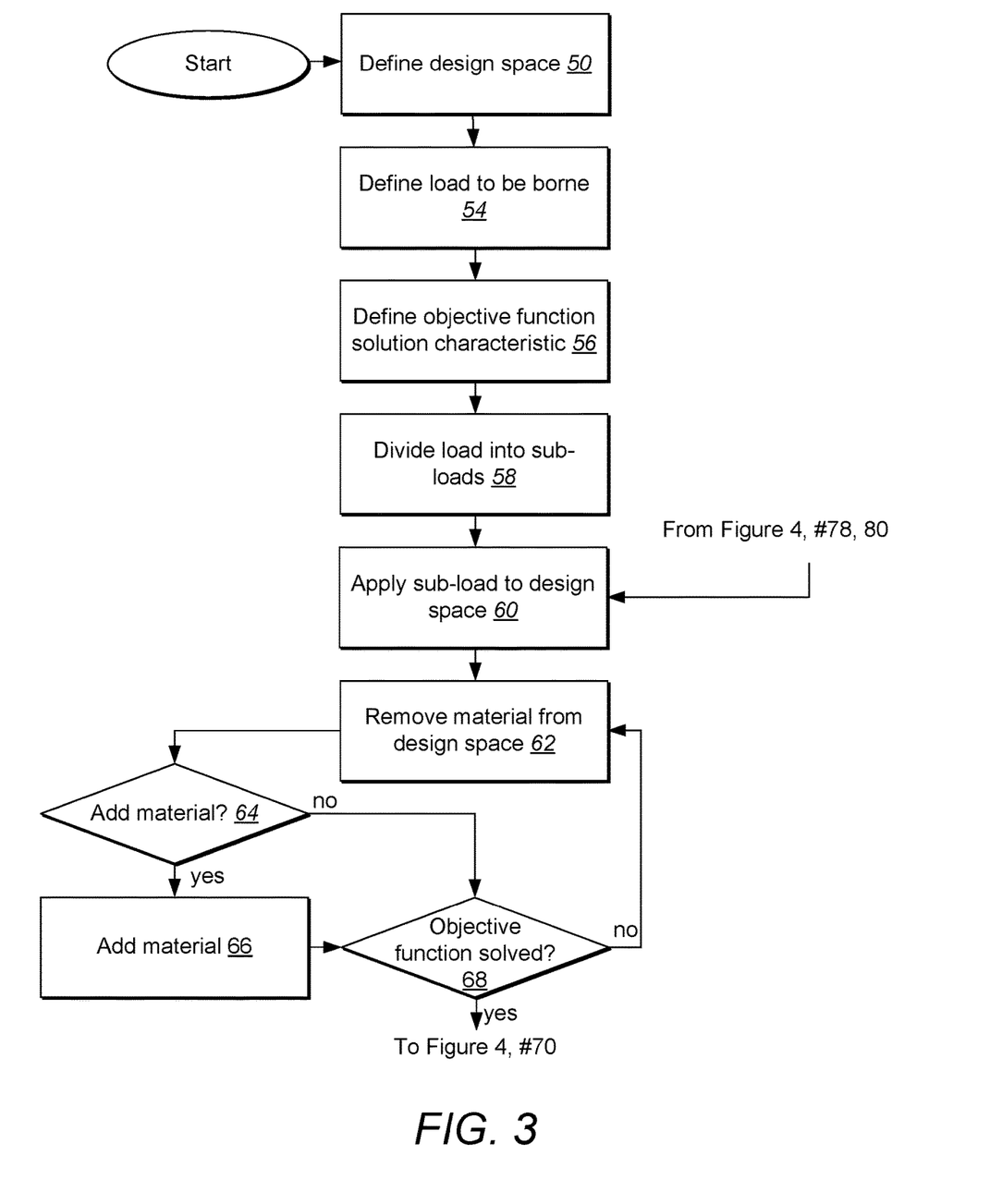
FIG. 3 shows steps of a method in accordance with embodiments of the invention.
Figure 5:
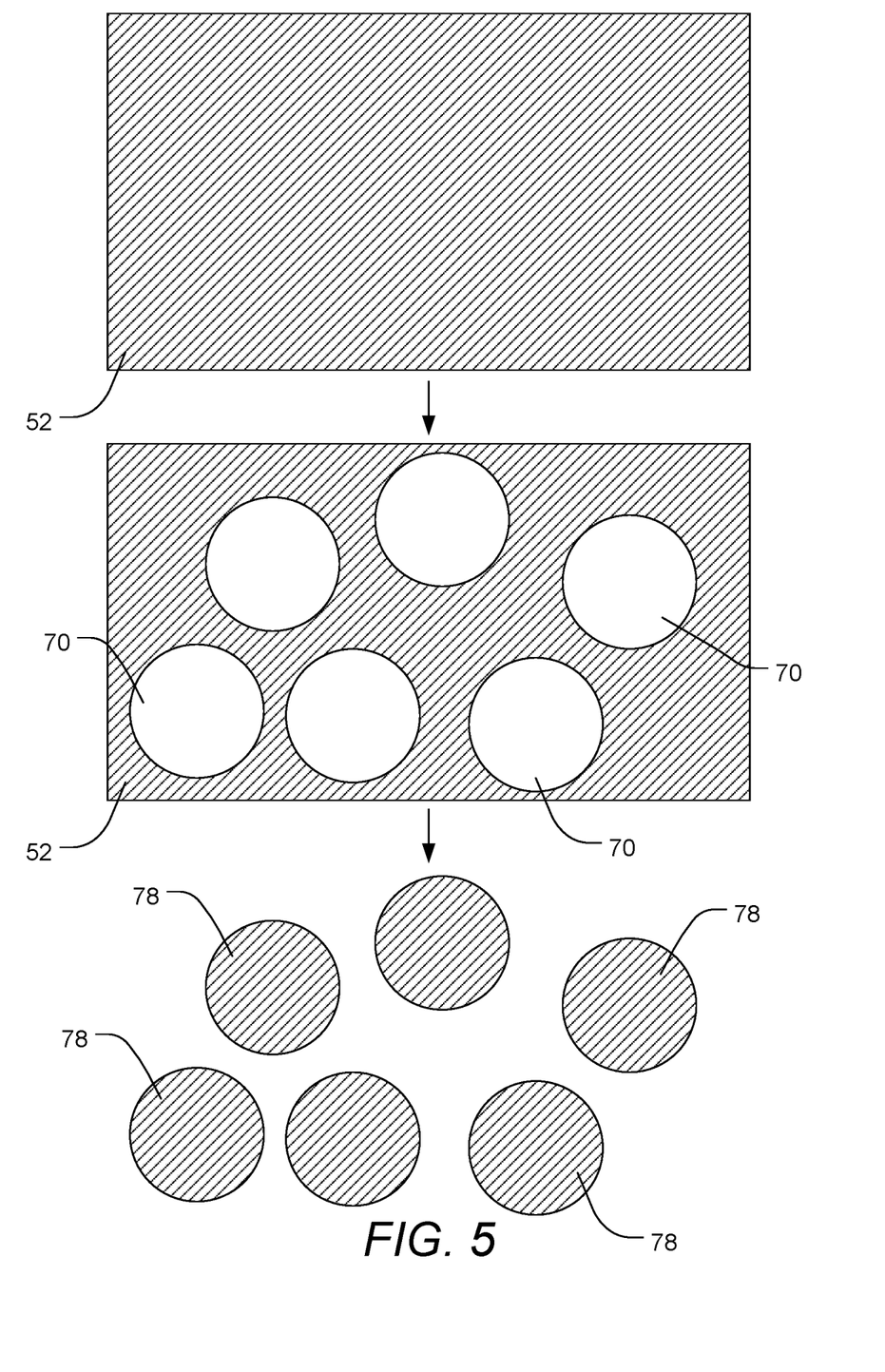
FIG. 5 illustrates a design space during execution of a method in accordance with certain embodiments of the invention.

FIG. 3 illustrates an exemplary embodiment of a method, which in exemplary embodiments is a computer-implemented method, for designing an implant in accordance with embodiments of the invention. According to exemplary embodiments of the invention, a method for designing an implant, particularly a porous implant such as an interbody spacer, begins with defining a design space at step 50. The design space, for example, may be defined by a volume which the implant is intended to occupy or may be defined by a portion of a volume which the implant is intended to occupy (e.g., a portion which is intended to be porous and have certain physical characteristics such as porosity (pore size and spacing), surface area, radiolucency, stress, stiffness, or the like). By way of example, FIG. 5 shows a conceptual view of a simplified example of a first design space 52 or volume represented as a rectangular volume. An actual design space may have any desirable shape or volume, and may include voids not included in the design space. Accordingly, the first design space 52 should be understood as being illustrated for purposes of discussion only, and not for purpose of limiting the scope of the claims.

The design space includes forces expected to be encountered by the implant (or the portion of the implant within the design space or design volume) as well as the material from which the implant is to be made (e.g., titanium, tantalum, titanium alloys, tantalum alloys, and the like). The material of the implant within the design space has bulk material properties that are known and that are taken into account when designing the implant as described herein.

The method continues at step 54 with a step of defining a load to be borne by the implant within the design space. By way of example, the load may be an expected load to be borne by the implant or the design volume of the implant. Then, at step 56, an objective function solution characteristic related to the design volume is defined or assigned to the design space or design volume. By way of example, the objective function characteristic may include maximizing or minimizing one or more characteristics such as stress, mass, radiolucency, surface area, or the like. Other objective functions are possible as desired, either in combination or singly.

The method continues as the defined load is divided into sub-loads at step 58. In some embodiments, the sub-loads are divided into even sub-loads. In other embodiments, the load is divided into uneven sub-loads. In some embodiments, uneven sub-loads may be applied to the design space in any desired order, such as from largest sub-load to smallest sub-load, from smallest sub-load to largest sub-load, or in random order. There is no particular limitation on the manner in which loads are divided or the order in which they are applied to the design space. Components of the original load are optionally held for additional cycles.

The method then continues as an optimization procedure is performed by solving the objective function with respect to the partial loads. The optimization procedure proceeds in several steps. First, at step 60, one of the sub-loads is applied to the material of the design space. Then, at step 62, material is removed from the design space in a manner to satisfy the objective function. Typically, this involves use of a computer to perform an analysis such as a finite element analysis or deriving a closed form solution. As part of this analysis, it may be necessary, as represented at decision block 64 and step 66, to add material back to the design space, such as when too much material has been removed at step 62. Execution proceeds to decision block 68, where a determination is made as to whether the objective function has been solved. If not, execution loops back to step 62, otherwise, execution proceeds to FIG. 4.

Figure 4:
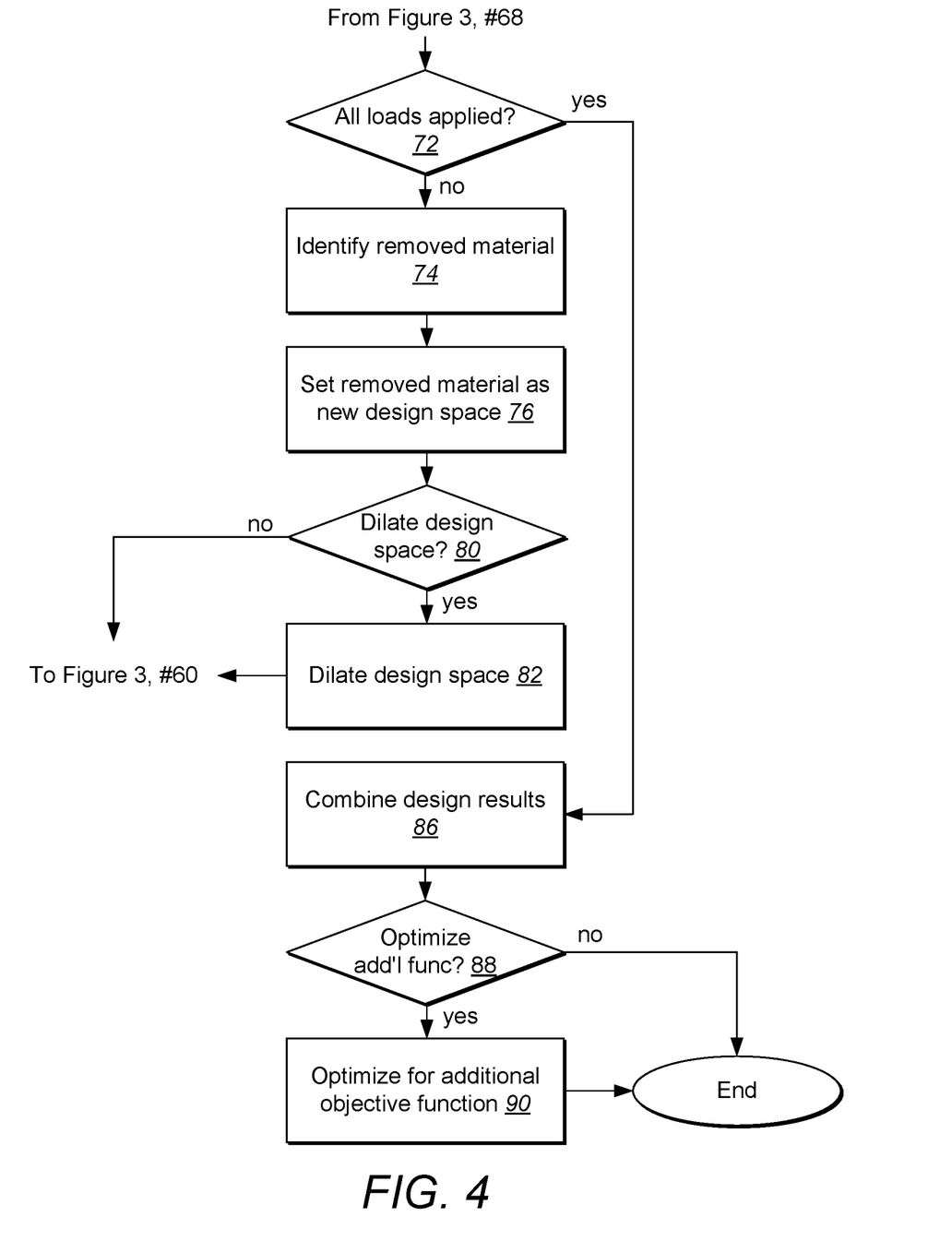
FIG. 4 shows steps of a method in accordance with embodiments of the invention.

When the objective function has been solved, only certain material remains in the design space, and the empty space may be illustrated as voids 70, as illustrated in the middle of FIG. 5. As may be appreciated, the voids 70 shown in FIG. 5 are not intended to depict any actual solution to any actual objective function, but are intended solely to facilitate the discussion of methods in accordance with embodiments of the invention. As illustrated in FIG. 4, execution of the method accordingly proceeds to decision block 72, where a determination is made as to whether all sub-loads have been applied. If not, the method proceeds to step 74, where the material removed in the previous steps is identified. Then, at step 76, the identified removed material is set as a new design space 78, as also illustrated at the bottom of FIG. 5.

Figure 6:
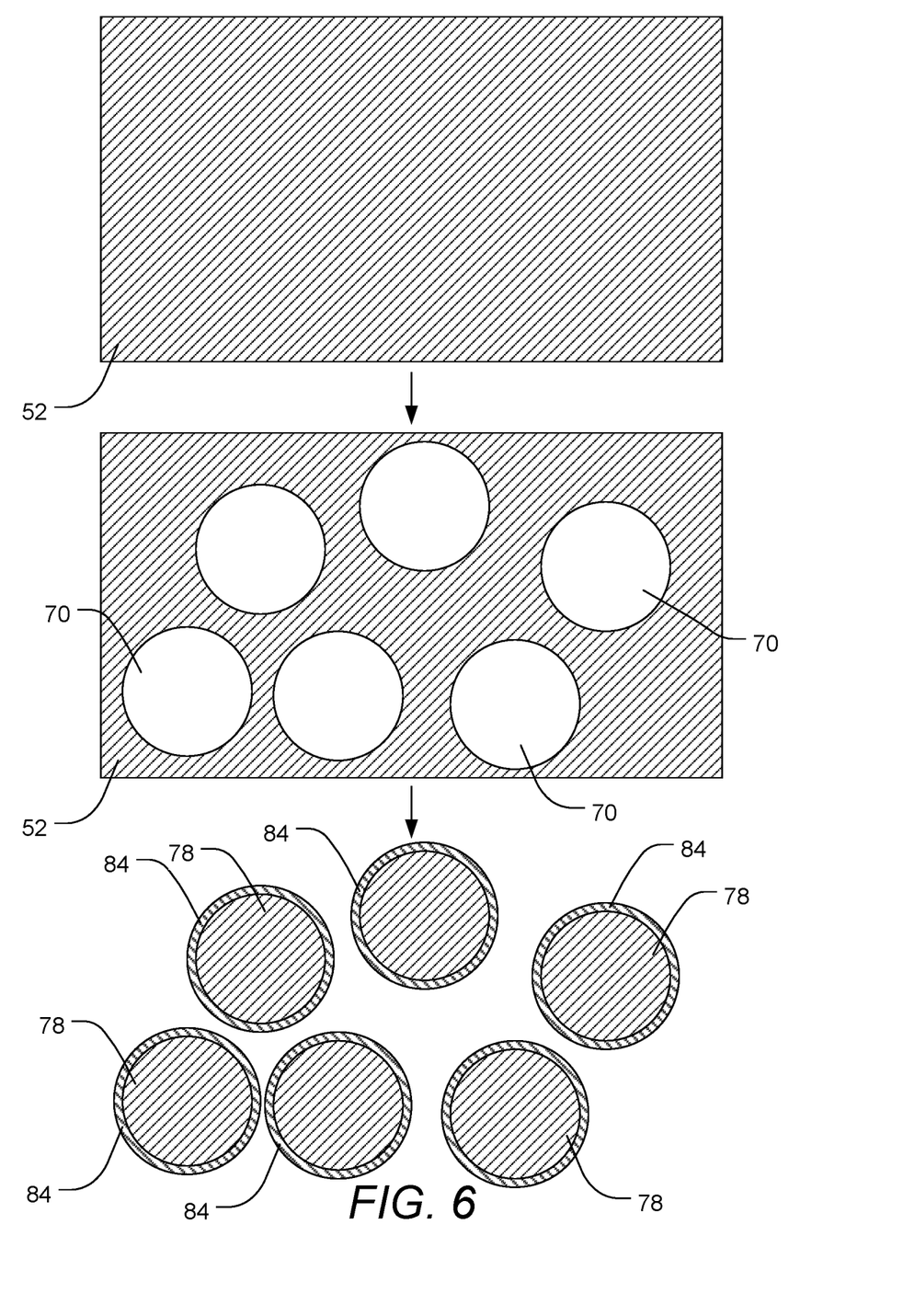
FIG. 6 illustrates a design space during execution of a method in accordance with certain embodiments of the invention.

Once a new design space is defined at step 76, a determination is made at decision block 80 whether to dilate the new design space 78. If a determination is made to dilate the new design space 78, execution proceeds to step 82 for dilation of the new design space 78. Dilation of the new design space 78 in some embodiments allows determination of contact interactions between the previous solution to the objective function and the new design space 78 (and thus the new solution to the objective function that is to be determined), thus maintaining solution continuity (such as maintaining a desired porosity across the solutions for the various sub-loads). Said differently, dilation of the new design space 78 creates a buffer region between iterative solutions to the various sub-loads to assure that solutions are continuous. FIG. 6 illustrates how the new design space 78 can be dilated to include a dilated design space 84.

Regardless of whether the new design space 78 is dilated or not at decision block 80 and step 82, execution of the method now returns to step 60 (in FIG. 3), where another sub-load is applied to the new design space 78 (and/or the dilated design space 84), and execution of the method proceeds as described such that a solution to the objective function is determined for the new sub-load. In this fashion, execution of the method loops until it is determined at decision block 72 (FIG. 4) that all sub-loads have been applied and solved, whereupon execution proceeds to step 86.

At step 86, the solutions to the various sub-loads are combined into a final design result. Then, execution of the method proceeds to decision block 88, where a determination is made as to whether to optimize an additional objective function. The additional objective function may be any objective function previously discussed, or other objective functions, such as weight, porosity, stress, surface area, or the like. If no other objective functions are to be optimized, execution of the method ends, and the design is complete. Alternatively, if another objective function is to be optimized, then execution proceeds to step 90, where another objective function can be optimized, using any desirable method, including methods as illustrated in FIGS. 3-4. Once the design is finished, the final design can be constructed, such as using a 3-dimensional printer that may be connected to the system (or to another computer system) as a peripheral device or the like.

In some embodiments, the design space 52 may be pre-divided allowing for two or more problems to be solved in parallel. In this fashion, the performance of the method to determine the solution and design can be improved. As desired, additional analyses for any of the steps may also be run in parallel to improve system performance or to better utilize system resources. In some embodiments, multiple solutions to the objective function or objective functions may be determined for each sub-load (or for varied application of sub-loads) to determine solutions providing optimal performance characteristics. Accordingly, there is no requirement that embodiments of the invention be limited to finding a single solution to any objective function nor is there any requirement that embodiments of the invention are limited to finding any "best" solution to any particular objective function.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A method for creating a porous implant, the method comprising:
   defining, by one or more processors, a first design volume to represent a porous implant, the first design volume comprising a material from which the porous implant is to be created;
   defining a load to be borne by the first design volume;
   defining an objective function solution characteristic related to the first design volume;
   dividing the load into a plurality of sub-loads including at least a first sub-load and a second sub-load;
   applying of the first sub-load to the first design volume;
   removing portions of the material from the first design volume to create first voids in the first design volume until the first design volume with the first voids satisfies the objective function solution characteristic with the first sub-load applied;
   defining the first voids in the first design volume as a second design volume, the second design volume also comprising the material from which the porous implant is to be created;
   applying the second sub-load to the second design volume;
   removing portions of the material from the second design volume to create second voids in the second design volume until the second design volume with the second voids satisfies the objective function solution characteristic with the second sub-load applied;
   combining the second design volume with the second voids with the first design volume with the first voids to create a final design of the porous implant; and
   creating the porous implant from the final design.

2. The method of claim 1, wherein a finite element analysis is performed to determine when the first design volume with the first voids and the second design volume with the second voids satisfy the objective function solution characteristic.

3. The method of claim 1, wherein a closed form solution is performed to determine when the first design volume with the first voids and the second design volume with the second voids satisfy the objective function solution characteristic.

4. The method of claim 1, wherein the objective function solution characteristic comprises maximizing or minimizing a characteristic selected from at least one of:
   stress;
   mass;
   surface area;
   radiolucency; and
   stiffness.

5. The method of claim 1, wherein defining the first voids in the first design volume as a second design volume comprises dilating the first voids.

6. The method of claim 1, further comprising performing a final evaluation and optimization for a different objective function.

7. The method of claim 6, wherein the different objective function comprises a function selected from at least one of weight, porosity, surface area, and stress.

8. One or more computer storage media storing computer executable instructions which when executed implement a method for creating a porous implant comprising:
   defining, by one or more processors, a first design volume to represent a porous implant, the first design volume comprising a material from which the porous implant is to be created;
   defining a load to be borne by the first design volume;
   defining an objective function solution characteristic related to the first design volume;
   dividing the load into a plurality of sub-loads including at least a first sub-load and a second sub-load;
   applying the first sub-load to the first design volume;
   removing portions of the material from the first design volume to create first voids in the first design volume until the first design volume with the first voids satisfies the objective function solution characteristic with the first sub-load applied;
   defining the first voids in the first design volume as a second design volume, the second design volume also comprising the material from which the porous implant is to be created;
   applying the second sub-load to the second design volume;
   removing portions of the material from the second design volume to create second voids in the second design volume until the second design volume with the second voids satisfies the objective function solution characteristic with the second sub-load applied;

combining the second design volume with the second voids with the first design volume with the first voids to create a final design of the porous implant; and creating the porous implant from the final design.

9. The computer storage media of claim 8, wherein a finite element analysis is performed to determine when the first design volume with the first voids and the second design volume with the second voids satisfy the objective function solution characteristic.

10. The computer storage media of claim 8, wherein a closed form solution is performed to determine when the first design volume with the first voids and the second design volume with the second voids satisfy the objective function solution characteristic.

11. The computer storage media of claim 8, wherein the objective function solution characteristic comprises maximizing or minimizing a characteristic selected from at least one of:
   stress;
   mass;
   surface area;
   radiolucency; and
   stiffness.

12. The computer storage media of claim 8, wherein defining the first voids in the first design volume as a second design volume comprises dilating the first voids.

13. The computer storage media of claim 8, wherein the method further comprises performing a final evaluation and optimization for a different objective function.

14. The computer storage media of claim 13, wherein the different objective function comprises a function selected from at least one of weight, porosity, surface area, and stress.

15. A method for creating a porous implant comprising:
   defining, by one or more processors, a first design volume to represent a porous implant, the first design volume comprising a material from which the porous implant is to be created;
   defining a load to be borne by the first design volume;
   defining an objective function solution characteristic related to the first design volume;
   dividing the load into a plurality of sub-loads including at least a first sub-load, a second sub-load and a third sub-load;
   applying the first sub-load to the first design volume;
   removing portions of the material from the first design volume to create first voids in the first design volume until the first design volume with the first voids satisfies the objective function solution characteristic with the first sub-load applied;
   defining the first voids in the first design volume as a second design volume, the second design volume also comprising the material from which the porous implant is to be created;
   applying the second sub-load to the second design volume;
   removing portions of the material from the second design volume to create second voids in the second design volume until the second design volume with the second voids satisfies the objective function solution characteristic with the second sub-load applied;
   defining the second voids in the second design volume as a third design volume, the third design volume also comprising the material from which the porous implant is to be created;
   applying the third sub-load to the third design volume;
   removing portions of the material from the third design volume to create third voids in the third design volume until the third design volume with the third voids satisfies the objective function solution characteristic with the third sub-load applied;
   combining the third design volume with the third voids, the second design volume with the second voids, and the first design volume with the first voids to create a final design of the porous implant; and
   creating the porous implant from the final design.

16. The method of claim 15, wherein defining the first voids in the first design volume as the second design volume comprises dilating the first voids.

17. The method of claim 15, wherein defining the second voids in the second design volume as the third design volume comprises dilating the second voids.

18. The method of claim 15, further comprising:
   prior to creating the porous implant from the final design, refining the final design to create a redefined final design by using a different objective function solution characteristic; and
   creating the porous implant from the refined final design.

19. The method of claim 18, wherein the objective function solution characteristic and the different objective function solution characteristic comprises maximizing or minimizing a characteristic selected from at least one of:
   stress;
   mass;
   surface area;
   radiolucency; and
   stiffness.

20. The method of claim 18, wherein creating the porous implant from the final design comprises 3D printing the porous implant from the final design.

* * * * *

UNITED STATES PATENT AND TRADEMARK OFFICE
CERTIFICATE OF CORRECTION

| | |
|---|---|
| PATENT NO. | : 11,833,267 B2 |
| APPLICATION NO. | : 16/813720 |
| DATED | : December 5, 2023 |
| INVENTOR(S) | : Peter Halverson and David T. Hawkes |

It is certified that error appears in the above-identified patent and that said Letters Patent is hereby corrected as shown below:

On the Title Page

Item (60) under Related U.S. Application Data, delete the paragraph and insert the following:
-- Provisional Application No. 62/815,256 filed on March 7, 2019. --

Signed and Sealed this
Thirteenth Day of May, 2025

Coke Morgan Stewart
*Acting Director of the United States Patent and Trademark Office*